(12) United States Patent
Markowitz et al.

(10) Patent No.: US 8,497,084 B2
(45) Date of Patent: Jul. 30, 2013

(54) 15-PGDH IN COLON CANCER

(75) Inventors: Sanford D. Markowitz, Pepper Pike, OH (US); Monica Bertagnolli, Newton, MA (US)

(73) Assignees: Case Western Reserve University, Cleveland, OH (US); The Brigham and Women's Hospital, Inc., Boston, MA (US)

( * ) Notice: Subject to any disclaimer, the term of this patent is extended or adjusted under 35 U.S.C. 154(b) by 315 days.

(21) Appl. No.: 12/774,641

(22) Filed: May 5, 2010

(65) Prior Publication Data

US 2010/0284989 A1 Nov. 11, 2010

Related U.S. Application Data

(60) Provisional application No. 61/215,505, filed on May 5, 2009.

(51) Int. Cl.
*C12Q 1/32* (2006.01)

(52) U.S. Cl.
USPC ............................................. 435/26; 435/4

(58) Field of Classification Search
USPC ........................................ 435/4, 26
See application file for complete search history.

(56) References Cited

PUBLICATIONS

Pichaud et al. "1,25-dihydroxyvitamin D3 induces NAD+-dependent 15-hydrosyprostaglandin dehydrogenase in human neonatal monocytes", Blood, 1997, 89(6):2105-2112.*

Cuzick et al. "Aspirin and non-sterodal anti-inflammatory drugs for cancer prevention: an international consensus statement" The Lancet, 2009, 10:501-507.*
Wakimoto et al., "Nonsteroidal anti-inflammatory drugs suppress glioma via 15-hydroxyprostaglandin dehydrogenase," Cancer Research, vol. 68(17), pp. 6978-6986 (2008).
Yan et al., "15-Hydroxyprostaglandin dehydrogenase inactivation as a mechanism of resistance to celecoxib chemoprevention of colon tumors," Proceedings of the National Academy of Sciences of the USA, vol. 106(23) pp. 9409-9413 (2009).
Yan et al., "15-Hydroxyprostaglandin dehydrogenase, a COX-2 oncogene antagonist, is a TGF-β-induced suppressor of human gastrointestinal cancers," Proceedings of the National Academy of Sciences of the USA, vol. 101(50), pp. 17468-17473 (2004).
Backlund et al., "15-Hydroxyprostaglandin Dehydrogenase Is Down-regulated in Colorectal Cancer," The Journal of Biological Chemistry, vol. 280(5), pp. 3217-3223 (2005).
Krishnan et al., "Inhibition of prostaglandin synthesis and actions contributes to the beneficial effects of calcitriol in prostate cancer," Dermato-Endocrinology, vol. 1(1), pp. 7-11 (2009).
Dalen, James E., "Aspirin to Prevent Heart Attack and Stroke: What's the Right Dose?", The American Journal of Medicine, vol. 119:198-202 (2006).

* cited by examiner

*Primary Examiner* — Bin Shen
(74) *Attorney, Agent, or Firm* — Ropes & Gray LLP

(57) ABSTRACT

The disclosure provides, among other things, a method of decreasing resistance to the chemopreventive properties of non-steroidal anti-inflammatory agents, e.g., celecoxib, particularly in the prevention of cancer, e.g., colon cancer, by increasing the levels or activity of 15-hydroxyprostaglandin dehydrogenase (15-PGDH). The disclosure also provides a method of identifying compounds that upregulate or reactivate 15-PGDH. The disclosure also provides a method of identifying an individual suitable for treatment with a non-steroidal anti-inflammatory agent in the treatment or prevention of colon cancer.

16 Claims, 5 Drawing Sheets

Celecoxib and 15-PGDH tissue levels in murine colonic mucosa

A

B

Celecoxib resistance in humans with low levels of 15-PGDH

15-PGDH IN COLON CANCER

RELATED APPLICATIONS

This application claims the benefit of priority to U.S. Provisional Application No. 61/215,505, filed May 5, 2009. The specification of the foregoing application is incorporated herein by reference in its entirety.

BACKGROUND

Colon cancer is the second leading cause of cancer-related death in the United States (Markowitz, S. D. (2007) *N Engl J Med* 356, 2195-8). An estimated 135,000 new cases of colon cancer occur each year. Although many people die of colon cancer, early stage colon cancers are often treatable by surgical removal (resection) of the affected tissue. Surgical treatment can be combined with chemotherapeutic agents to achieve an even higher survival rate in certain colon cancers. However, the survival rate drops to 5% or less over five years in patients with metastatic (late stage) colon cancer. Additionally, systemic therapies in combination with chemotherapies have been developed for the treatment of colon cancer. However, no therapies have exhibited sufficient anti-tumor activity to prolong the survival of colon cancer patients with metastatic disease with any degree of reliability.

Strategies for preventing colon cancer have focused on preventing development of colonic adenomas, the premalignant tumors that are the precursors of invasive colon cancers (Markowitz, S. D. (2007) *N Engl J Med* 356, 2195-8). For example, pharmacologic approaches have targeted the inhibition of COX-2, an enzyme that mediates conversion of arachidonic acid to bioactive prostaglandins, and whose expression is markedly increased in colon cancers (Markowitz, S. D. (2007) *N Engl J Med* 356, 2195-8; Cha, Y. I. & DuBois, R. N. (2007) *Annu Rev Med* 58, 239-52). Inhibitors of COX-2 such as nonsteroidal anti-inflammatory drugs (NSAID) have been shown to decrease colon adenoma development in individuals with Familial Adenomatous Polyposis (Steinbach, G. et al. (2000) *N Engl J Med* 342, 1946-52). For example, in individuals with non-familial sporadic colon adenomas, celecoxib reduces by 33-45% the risk of developing future adenomas, and by 57-64% the risk of developing adenomas with advanced histology (Arber, N. et al., (2006) *N Engl J Med* 355, 885-95; Bertagnolli, M. M. et al., (2006) *N Engl J Med* 355, 873-84). However, a significant proportion of individuals demonstrate resistance to the colon tumor prevention activity of NSAIDs, and the molecular mechanism underlying this resistance is largely unknown. Accordingly, a need still exists to develop methods for the successful treatment of colorectal carcinoma.

SUMMARY OF THE INVENTION

In one aspect, the present invention provides a method of identifying subjects who would be responsive to non-steroidal inflammatory drug (NSAID) therapy, comprising: (i) obtaining a biological sample from said subject; and (ii) measuring 15-PGDH levels or 15-PGDH activity, wherein normal or increased level or activity of 15-PGDH indicates that the subject would be responsive to NSAID therapy.

In certain embodiments, the 15-PGDH level or 15-PGDH activity is compared to a reference level or activity of 15-PGDH. In one embodiment, the reference level or activity of 15-PGDH is measured from a healthy subject, or a subject known to be responsive to NSAID therapy. In one embodiment, the NSAID therapy prevents or treats colon neoplasia, e.g., colon adenoma or colon cancer. In other embodiments, the NSAID therapy treats pain disorders, inflammatory disorders, and immunologic disorders.

In some embodiments, said NSAID is celecoxib or aspirin.

In one embodiment, the sample is a colonic tissue. In some embodiments, the sample is a bodily fluid selected from blood, serum, plasma, a blood-derived fraction, stool, urine, and a colonic effluent. In other embodiments, the blood-derived fraction comprises peripheral blood leukocytes.

In certain embodiments, the level measured in the foregoing method is a protein, mRNA, or cDNA level of 15-PGDH.

In another aspect, the present invention provides a method of determining whether a subject is predisposed to developing resistance to an NSAID therapy, comprising: (i) obtaining a biological sample from said subject; and (ii) measuring 15-PGDH levels or 15-PGDH activity; wherein a reduced level or activity of 15-PGDH in the subject relative to a reference sample indicates that the subject is predisposed to developing resistance in the NSAID therapy.

In any of the foregoing aspects and embodiments, the method further comprises (i) obtaining a reference biological sample from a normal subject; (ii) measuring levels of 15-PGDH or its activity; and (iii) comparing said levels or activity in the sample from the subject to levels or activity in a normal sample.

In certain embodiments, the NSAID therapy prevents or treats colon neoplasia, e.g., colon adenoma or colon cancer. In other embodiments, the NSAID therapy treats pain disorders, inflammatory disorders, and immunologic disorders.

In some embodiments, the NSAID is celecoxib or aspirin.

In other embodiments, the sample comprises a colonic tissue. In other embodiments, the sample is a bodily fluid selected from the group consisting of: blood, serum, plasma, a blood-derived fraction, stool, urine, and a colonic effluent. Exemplary blood-derived fraction includes peripheral blood leukocytes.

In some embodiments, the level measured in the foregoing method is selected from a protein, mRNA, or cDNA of 15-PGDH.

In other aspects, the present invention provides a method of treating an NSAID-responsive condition comprising administering an effective amount of an NSAID and an agent that upregulates 15-PGDH. In certain embodiments, the agent is not a Prox-1 suppressor.

In certain embodiments, the NSAID-responsive condition is prevention or treatment of colon neoplasia, e.g., colon cancer or colon adenoma. In other embodiments, the NSAID-responsive condition is selected from the group consisting of: pain disorders, inflammatory disorders, or immunologic disorders.

In some embodiments, the NSAID is celecoxib or aspirin.

In certain embodiments, the agent is selected from the group consisting of: a small molecule, a polypeptide, nucleic acid, aptamers, or antibody. Exemplary small molecules include erlotinib or butyrate. In one embodiment, the nucleic acid is an siRNA or antisense. In certain embodiments, the siRNA inhibits the expression of beta-catenin transcription factor. In other embodiments, the agent directly or indirectly upregulates 15-PGDH levels or activity.

In another aspect, the present invention provides a method of decreasing NSAID resistance in a patient, comprising administering: (i) an effective amount of a compound that increases 15-PGDH levels or 15-PGDH activity; or (ii) an effective amount of 15-PGDH protein, cDNA, or an active fragment thereof. In certain embodiments, a compound that increases 15-PGDH levels is not a Prox-1 suppressor.

In certain embodiments, the levels include protein, mRNA, or cDNA level of 15-PGDH. In one embodiment, the compound is selected from the group consisting of: a small molecule, a polypeptide, a nucleic acid, an aptamer, or an antibody. Exemplary nucleic acids include an siRNA or antisense. In one embodiment, the siRNA inhibits the expression of beta-catenin transcription factor. In certain embodiments, the compound directly or indirectly upregulates 15-PGDH levels or activity.

In other aspects, the present invention provides a method of screening for test agents that would decrease non-steroidal inflammatory drug (NSAID) resistance, comprising: contacting cells with said test agent; and measuring 15-PGDH levels or 15-PGDH activity, wherein an increase in 15-PGDH level or activity indicates that said agent is a candidate agent that decreases NSAID resistance.

In some embodiments, the 15-PGDH level is compared to a reference cell.

In certain embodiments, the test agent is selected from the group consisting of: a small molecule, a polypeptide, nucleic acid, aptamers, and antibody. In exemplary embodiments, the nucleic acid is an siRNA or antisense. In one embodiment, the test agent directly or indirectly upregulates 15-PGDH levels or activity.

In one aspect, the present invention provides a method of identifying a subject who is at risk for developing colon neoplasia, comprising: (i) obtaining a colon tissue sample from said subject; and (ii) measuring 15-PGDH levels or 15-PGDH activity, wherein a level or activity of 15-PGDH that is less than 50% of the level or activity of 15-PGDH from a healthy population indicates that the subject is at risk for developing colon neoplasia. In certain embodiments, the level or activity of 15-PGDH from the subject sample is less than 90%, 80%, 70%, 65%, 60%, 55%, 50%, 45%, 40%, 35%, 30%, 25%, 20%, 15%, 10%, or 5% of the level or activity of 15-PGDH determined from a healthy population. As described herein, the level of 15-PGDH is a value of an amount of 15-PGDH protein or nucleic acid measured as a quantified unit. In certain embodiments, the activity of 15-PGDH is a measured unit of enzymatic activity of 15-PGDH on a known substrate, e.g., $PGE_2$. In other embodiments, such levels are average values measured from a pool of a healthy population.

In some embodiments, the biological sample is selected from the group consisting of whole blood or a fraction thereof. In other embodiments, said biological sample is selected from the group consisting of urine or stool samples. In certain embodiments, the biological sample is a blood sample. In certain embodiments, the sample is a non-neoplastic sample. In one embodiment, the blood sample is fractionated to obtain blood serum and/or blood plasma. In other embodiments, the biological sample is colonic tissue. In one embodiment, said biological sample is enriched for 15-PGDH. In some embodiments, the level is protein, mRNA or cDNA level of 15-PGDH.

In one embodiment, the 15-PGDH level is detected by an assay. In one exemplary method, the assay employs an antibody. In one embodiment, the antibody is detectably labeled, e.g., an enzyme, a fluorescent substance, a chemiluminescent substance, a chromophore, a radioactive isotope and a complexing agent. In other embodiments, the assay is selected from an immunoprecipitation assay, a Western blot, a radioimmunoassays, an enzyme-linked immunosorbent assay (ELISA), and PCR.

In one aspect, the present invention provides a kit for detecting colon neoplasia in a biological sample, comprising: a) an antibody which interacts with an epitope of 15-PGDH; and b) instructions for use. In one embodiment, said antibody is detectably labeled, e.g., an enzyme, a fluorescent substance, a chemiluminescent substance, a chromophore, a radioactive isotope and a complexing agent.

In another aspect, the present invention provides a kit for detecting colon neoplasia in a biological sample, comprising: a) a primer capable of amplifying 15-PGDH nucleic acid; and b) instructions for use.

DETAILED DESCRIPTION

Definitions

Figure 1A:
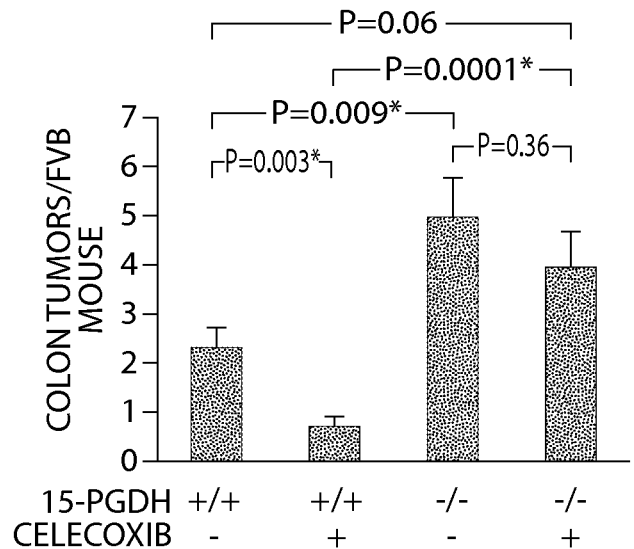
FIG. 1: Celecoxib resistance in 15-PGDH knockout mice. (A) AOM induced colon tumor development in 15-PGDH +/+ FVB mice untreated (−) (n=16) or treated (+) (n=12) with celecoxib, versus FVB 15-PGDH −/− mice untreated (n=13) or treated (n=17) with celecoxib. P-values represent comparisons of tumor numbers between groups, with * indicating statistically significant values. Error bars designate standard error of the mean. (B) AOM induced development of large colon tumors (diameter>1 mm) in the same mice cohorts graphed in panel A). (C) Gross morphology of representative colons from AOM treated 15-PGDH +/+ and −/− mice administered celecoxib containing (+) or celecoxib free (−) diets. Arrows designate colon tumors. (D) Colonic mucosal $PGE_2$ levels (ng/mg protein) in 15-PGDH +/+ FVB mice untreated (−) (n=10) or treated (+) (n=9) with celecoxib, versus FVB 15-PGDH −/− mice untreated (n=12) or treated (n=11) with celecoxib.

For convenience, certain terms employed in the specification, examples, and appended claims are collected here.

Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

As used herein, the phrase "gene expression" or "protein expression" includes any information pertaining to the amount of gene transcript or protein present in a sample, as well as information about the rate at which genes or proteins are produced or are accumulating or being degraded (eg. reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The term "detection" or "measuring" is used herein to refer to any process of observing a marker, in a biological sample, whether or not the marker is actually detected. In other words, the act of probing a sample for a marker is a "detection" or "measurement" even if the marker is determined to be not present or below the level of sensitivity. Detection or measurement may be a quantitative, semi-quantitative or non-quantitative observation.

The terms "healthy", "normal" and "non-neoplastic" are used interchangeably herein to refer to a subject or particular cell or tissue that is devoid (at least to the limit of detection) of a disease condition, such as a neoplasia, that is associated with colon cancer. These terms are often used herein in reference to tissues and cells of the colon. Thus, for the purposes of this application, a patient with severe heart disease but lacking a colorectal cancer-associated disease would be termed "healthy".

As used herein, a "reference sample" is a sample derived from a healthy, normal, or non-neoplastic subject.

The term "including" is used herein to mean, and is used interchangeably with, the phrase "including but not limited to".

As used herein, the term "nucleic acid" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

"Treating" a condition or disease refers to curing as well as ameliorating at least one symptom of the condition or disease.

The term "prophylactic" or "therapeutic" treatment is art-recognized and refers to administration of a drug to a host. The terms "prophylactic" and "therapeutic" is used interchangeably with "prevent"/"prevention" and "treat"/treatment, respectively. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "preventing" is art-recognized, and when used in relation to a condition, such as a local recurrence (e.g., pain), a disease such as cancer, or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "or" is used herein to mean, and is used interchangeably with, the term "and/or", unless context clearly indicates otherwise.

The terms "polypeptide" and "protein" are used interchangeably herein.

The term "purified protein" refers to a preparation of a protein or proteins which are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

A therapeutically "effective" amount means an amount of agent effective to prevent, alleviate or ameliorate symptoms of disease or prolong the survival of the subject being treated. Therapeutically effective dosages may be determined by using in vitro and in vivo methods, such as those described herein.

A "recombinant nucleic acid" is any nucleic acid that has been placed adjacent to another nucleic acid by recombinant DNA techniques. A "recombinant nucleic acid" also includes any nucleic acid that has been placed next to a second nucleic acid by a laboratory genetic technique such as, for example, transformation and integration, transposon hopping or viral insertion. In general, a recombined nucleic acid is not naturally located adjacent to the second nucleic acid.

The term "recombinant protein" refers to a protein that is produced by expression from a recombinant nucleic acid.

A "subject" is any organism of interest, generally a mammalian subject, such as a mouse, and preferably a human subject.

As used herein, the term "NSAID" includes, but is not limited to, those agents which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), such as the commercially available NSAIDs aceclofenac, acemetacin, acetaminophen, acetaminosalol, acetyl-salicylic acid (aspirin), acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lomoxicam, loxoprofen, meclofenamic acid, mefenamic acid, meloxicam, mesalamine, metiazinic acid, mofezolac, montelukast, mycophenolic acid, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, resveratrol, salacetamide, salicylamide, salicylamide-O-acetyl acid, salicylsulphuric acid, salicin, salicylamide, salsalate, sulindac, suprofen, suxibutazone, tamoxifen, tenoxicam, theophylline, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast, rofecoxib and cyclosporine. Additionally, The Merck Manual, 16th Edition, Merck Research Laboratories (1990) pp 1308-1309, as well as The Pharmacological Basis of Therapeutics, 9th edition, Macmillan Publishing Co., 1996, pp 617-655, provide well known examples of NSAIDs.

As used herein, conditions that are responsive to NSAID treatment (also "NSAID-responsive conditions") refers to any disease, disorder or condition that may be treated in a subject in need thereof with NSAID administration. NSAID-responsive conditions also include colon neoplasia including, but not limited to, colon adenoma and colon cancer therapy and prevention, as described herein. Additional examples of NSAID-responsive diseases and disorders include, but are not limited to, pain and inflammation.

In some embodiments, an "NSAID-responsive condition" also refers to a condition that is NSAID-resistant, but that becomes NSAID-responsive as a result of the methods disclosed herein. For example, the present disclosure is useful for treating an "NSAID-responsive condition" according to the methods described herein, even though the condition is in fact NSAID-resistant. That is, the methods disclosed herein turns an NSAID-resistant condition into an NSAID-responsive condition. Accordingly, it should be understood that "NSAID-responsive" refers to an NSAID-resistant condition that can be made NSAID-responsive.

Additionally, the present method can be used to treat an NSAID-responsive condition or subject in which the subject is already NSAID-responsive. For example, the subject may be relatively unresponsive to NSAID therapy, but not completely resistant. In other embodiments, the present method can be used to treat a subject who is already NSAID-responsive, but may benefit from the present invention.

As described herein, "NSAID-resistant" refers to a subject whose 15-PDGH level or activity is a fraction (or percentage) of the average 15-PDGH level or activity measured in a healthy population. The level or activity of 15-PGDH from an NSAID-resistant subject sample is less than 90%, 80%, 70%, 65%, 60%, 55%, 50%, 45%, 40%, 35%, 30%, 25%, 20%, 15%, 10%, or 5% of the level or activity of 15-PGDH determined from a healthy population. As described herein, the level of 15-PGDH is a value of an amount of 15-PGDH protein or nucleic acid measured as a quantified unit. In certain embodiments, the activity of 15-PGDH is a measured unit of enzymatic activity of 15-PGDH on a known substrate, e.g., $PGE_2$. In other embodiments, such levels are average values measured from a pool of a healthy population.

As used herein, the term "pain" includes all types of pain. Pain includes, but is not limited to, chronic pain, such as arthritis pain (e.g., pain associated with osteoarthritis and rheumatoid arthritis), neuropathic pain, and post-operative pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term also refers to nociceptive pain or nociception. The term also refers to persistent pain, such as, but not limited to, neuropathic pain, diabetic neuropathy, fibromyalgia, pain associated with somatoform disorders, arthritic pain, cancer pain, neck pain, shoulder pain, back pain, cluster headaches, tension-type headache, migraine, herpes neuralgia, phantom limb pain, central pain, dental pain, pain traditionally resistant to treatment with NSAIDs, and post-operative pain. The term pain also refers to the pain associated with the inflammation-related diseases and disorders described herein.

The term "inflammation" and "inflammation-related disease and disorder" will be understood by those skilled in the art to include any condition characterized by a localized protective response elicited by injury or destruction of tissues resulting from any of the causes mentioned hereinbefore, and which is manifest by heat, swelling, pain, redness, dilation of blood vessels and/or increased blood flow, invasion of the affected area by white blood cells, loss of function and/or any other symptoms known to be associated with the inflammatory condition. The term will thus be understood to include, inter alia, acute, chronic, ulcerative, specific, allergic and necrotic inflammation, as well as all other forms of inflammation known to those skilled in the art. The term also includes arthritis (including osteoarthritis and rheumatoid arthritis), inflammatory bowel disease, eczema, psoriasis, atopic dermatitis, psoriatic arthropathy and asthma, post operative inflammation, dental inflammation, acute and chronic ocular inflammatory diseases, conjunctivitis. The compounds and compositions of the subject invention advantageously can block the immunogenic inflammatory pathway, thereby providing a method for inhibiting immunogenic inflammation. Accordingly, the subject compounds and compositions can be useful in the treatment of neurogenic inflammation, present in different processes, such as diabetes, asthma, cystitis, gingivitis, migraine, dermatitis, rhinitis, psoriasis, inflammation of sciatic and lumbar nerves, gastrointestinal processes, ocular inflammation, and acute allergic response, asthma, rheumatoid arthritis, osteoarthritis and other inflammatory conditions involving acute and/or chronic joint inflammation in a subject, preferably mammalian, more preferably human.

Overview

It has been shown that 15-prostaglandin dehydrogenase (also known as 15-hydroxyprostaglandin dehydrogenase; 15-PGDH), a prostaglandin degrading enzyme, functions as an endogenous inhibitor of the colonic COX-2 pathway and as a colon tumor suppressor gene (Yan, M. et al., (2004) *Proc Natl Acad Sci USA* 101, 17468-73; Myung, S. J. et al., (2006) *Proc Natl Acad Sci USA* 103, 12098-102). 15-PGDH is highly expressed in normal colon mucosa, but expression is ubiquitously lost in human colon cancers (Yan, M. et al., (2004) *Proc Natl Acad Sci USA* 101, 17468-73; Backlund, M. G. et al., (2005) *J Biol Chem* 280, 3217-23). Knocking out the murine 15-PGDH gene markedly sensitizes colon tumor induction by the carcinogen azoxymethane (AOM) in normally resistant C57BL/6J mice (Myung, S. J. et al., (2006) *Proc Natl Acad Sci USA* 103, 12098-102).

The disclosure provided herein shows, in part, that the adenoma prevention activity of the COX-2 inhibitor celecoxib requires the concomitant presence of the 15-prostaglandin dehydrogenase (15-PGDH) tumor suppressor gene, and that loss of 15-PGDH expression imparts resistance to celecoxib's anti-tumor effects. For example, the adenoma preventive activity of celecoxib is abrogated in mice genetically lacking 15-PGDH. In FVB mice, celecoxib prevents 85% of azoxymethane (AOM) induced tumors>1 mm in size, but is essentially inactive in preventing tumor induction in 15-PGDH null animals. Indeed, celecoxib treated 15-PGDH null animals develop more tumors than do celecoxib naïve wild-type mice. In parallel with the loss of tumor prevention activity, celecoxib-mediated suppression of colonic PGE2 levels is also markedly attenuated in 15-PGDH null versus wild-type mice. Additionally, as predicted by the murine models, humans with low colonic 15-PGDH levels also demonstrate celecoxib resistance. Specifically, in a colon adenoma prevention trial, in all cases tested, individuals who developed new adenomas while on celecoxib treatment were also found as having low colonic 15-PGDH. Finally, because drugs that inhibit COX activity are among the most common medications prescribed for relief of pain and inflammation, it is contemplated that low 15-PGDH levels also impart clinical resistance to these therapeutic activities and, therefore, the therapeutic benefits of increasing 15-PGDH can be extended beyond cancer therapy.

The interactions between pharmacologic regulation of colonic prostaglandins by celecoxib and the genetic regulation of colonic prostaglandins by 15-PGDH are disclosed herein. Pharmacologic inhibitors of the prostaglandin-synthesizing COX-2 oncogene prevent the development of pre-malignant human colon adenomas. Resistance to treatment, however, is common. Accordingly, the invention relates, in part, to a method of identifying subjects who would be responsive to non-steroidal inflammatory drug (NSAID) therapy, comprising: (i) obtaining a biological sample from said subject; and (ii) measuring 15-PGDH levels or 15-PGDH activity, wherein normal or increased level or activity of 15-PGDH indicates that the subject would be responsive to NSAID therapy. The subject may be a subject at risk of developing colon neoplasia (e.g., based on family history), or a subject at risk of colon adenoma relapse. Further, the subject may be any patient who is undergoing or about to undergo NSAID therapy for any NSAID-responsive condition. That is, the subject may be one who is about to undergo NSAID therapy, and the method disclosed herein may be used to determine whether the subject will benefit from the NSAID therapy (i.e., determines if the subject might be resistant to NSAID therapy).

Another aspect of the invention relates to a method of determining whether a subject is predisposed to developing NSAID resistance in a therapy, comprising: (i) obtaining a biological sample from said subject; and (ii) measuring 15-PGDH levels or 15-PGDH activity, wherein a reduced level or activity of 15-PGDH in the subject relative a normal sample indicates that the subject is predisposed to developing NSAID resistance in the therapy. The normal sample may be derived from a healthy subject. Alternatively, the reference sample may be derived from a subject who has previously suffered from colon neoplasia, but has undergone NSAID therapy with no colon adenoma relapse (i.e., a subject responsive to NSAID therapy). For any of these reference values, one of ordinary skill in the art would understand that the value may be a mean or median of a representative pool of subjects.

Another aspect of the invention relates to a method of treating any NSAID-responsive condition comprising administering an effective amount of an NSAID and an agent that upregulates 15-PGDH. In particular, the method of treating an NSAID-responsive condition applies to a subject who is NSAID-resistant or a subject who, through the methods described herein, was determined to be resistant to NSAID therapy.

Another aspect of the invention relates to a method of decreasing NSAID resistance in a patient, comprising administering: (i) an effective amount of a compound that increases 15-PGDH levels or 15-PGDH activity; or (ii) an effective amount of 15-PGDH protein, cDNA, or an active fragment thereof. The patient may be a subject at risk of developing colon neoplasia (e.g., based on family history), or a subject at risk of colon adenoma relapse, but is suspected of being resistant to NSAID therapy. Further, the patient may be any subject who is undergoing or about to undergo NSAID therapy for any NSAID-responsive condition, but who experiences NSAID resistance.

In one aspect, the present invention provides a method of identifying a subject who is at risk for developing colon neoplasia, comprising: (i) obtaining a non-neoplastic sample from said subject; and (ii) measuring 15-PGDH levels or 15-PGDH activity, wherein a level or activity of 15-PGDH that is less than 50% of the level or activity of 15-PGDH from a healthy population indicates that the subject is at risk for developing colon neoplasia. The normal sample as disclosed herein may be derived from a healthy subject. Alternatively, the normal sample may be derived from a subject who has previously suffered from colon neoplasia, but has undergone NSAID therapy with no colon adenoma relapse (i.e., a subject responsive to NSAID therapy). For any of these normal reference values, one of ordinary skill in the art would understand that the value may be a mean or median of a representative pool of subjects.

One of ordinary skill in the art will recognize that the foregoing aspects and embodiments may be combined.

Measurement/Detection of 15-PGDH

In certain embodiments, the invention provides methods for detecting molecular markers, such as proteins or nucleic acid transcripts of 15-PGDH described herein. In certain embodiments, a method of the invention comprises providing a biological sample and probing the biological sample for the presence of a 15-PGDH. Information regarding the presence or absence of 15-PGDH, and optionally the quantitative level of 15-PGDH, may then be used to draw inferences about the nature of the biological sample and, if the biological sample was obtained from a subject, the health state of the subject.

Samples for use with the methods described herein may be essentially any biological material of interest. For example, a sample may be a tissue sample from a subject, a fluid sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a colon cancer from a first subject, e.g. a human, that has been cultured in a second subject, e.g. an immunocompromised mouse). In certain embodiments, the sample is colon/rectal tissue, e.g., ascending colon, transverse colon, descending colon, sigmoid colon, or redundant colon.

The term "sample" as used herein is intended to encompass both a biological material obtained directly from a subject (which may be described as the primary sample) as well as any manipulated forms or portions of a primary sample. For example, in certain embodiments, a fluid sample may be a blood sample. In this case, the term sample is intended to encompass not only the blood as obtained directly from the patient but also fractions of the blood, such as plasma, serum, cell fractions (e.g. platelets, erythrocytes, lymphocytes), protein preparations, nucleic acid preparations, etc. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc. In certain embodiments, a fluid sample may be a urine sample. In certain embodiments, a preferred solid or semi-solid sample may be a stool sample. In certain embodiments, a preferred tissue sample may be a biopsy from a tissue known to harbor or suspected of harboring a colon neoplasia. In certain embodiments, a preferred cell culture sample may be a sample comprising cultured cells of a colon cancer cell line, such as a cell line cultured from a metastatic colon cancer tumor or a colon-derived cell line lacking a functional TGF-β, TGF-β receptor or TGF-β signaling pathway. A subject is preferably a human subject, but it is expected that the molecular markers disclosed herein, and particularly their homologs from other animals, are of similar utility in other animals. In certain embodiments, it may be possible to detect a marker directly in an organism without obtaining a separate portion of biological material. In such instances, the term sample is intended to encompass that portion of biological material that is contacted with a reagent or device involved in the detection process.

In certain aspects, samples of the subject methods can be collected from patients. These patients may be subjects who have been determined to have a high risk of having a condition of interest based on their personal or family history. Other patients include subjects who are known to have an NSAID-responsive condition and for whom the test is being used to determine the effectiveness of therapy or treatment they are receiving. Also, samples could be collected from healthy subjects who are having a test as part of a routine examination, or to establish baseline levels (e.g., a control or reference level) of the biomarker. Alternatively, samples could be collected from subjects who are known to be responsive to NSAID therapy.

Samples should generally be prepared in a manner that is consistent with the detection system to be employed. For example, a sample to be used in a protein detection system should generally be prepared in the absence of proteases Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

Assays can be used to determine presence or absence of a marker (e.g., mRNA or protein) in a sample as well as the quantity of a marker in a sample. The amount of the marker can be determined by comparing to a standard. A standard can be, e.g., an amount or level known to be present or predetermined in a control sample (e.g., a healthy subject, a subject already responsive to NSAID therapy who does not require the disclosed methods, or a subject who has successfully undergone an NSAID therapy, i.e., a subject responsive to NSAID therapy). It is understood that the test amount of the marker need not be measured in absolute units, as long as the unit of measurement can be compared relative to a control.

Measurement/Detection of Polynucleotides of 15-PGDH

Those of skill in the art will recognize that the measurement or detection of the expression of 15-PGDH polynucleotides has many uses. For example, as discussed herein, measuring the 15-PGDH levels in a patient is useful for diagnosing colon cancer, or determining whether a subject is predisposed to developing colon cancer. Additionally, measuring the 15-PGDH levels in a subject is useful for determining whether the subject may benefit from the colon cancer preventive properties of NSAIDs. The subject in question may already be afflicted with colon cancer, or the subject may be at risk of developing colon cancer. In some embodiments, the subject was previously afflicted with colon cancer and is in a state of remission. Moreover, as described herein, detection of gene expression is useful to identify modulators of 15-PGDH expression.

In certain embodiments, a method of the invention comprises detecting the presence of a 15-PGDH nucleic acid, such as an mRNA, in a sample. Optionally, the method involves obtaining a quantitative measure of the expressed nucleic acid in the sample. In view of this specification, one of skill in the art will recognize a wide range of techniques that may be employed to detect and optionally quantify the presence of a nucleic acid. Nucleic acid detection systems generally involve preparing a purified nucleic acid fraction of a sample, and subjecting the sample to a direct detection assay or an amplification process followed by a detection assay. Amplification may be achieved, for example, by polymerase chain reaction (PCR), reverse transcriptase (RT) and coupled RT-PCR. Detection of a nucleic acid is generally accomplished by probing the purified nucleic acid fraction with a probe that hybridizes to the nucleic acid of interest, and in many instances detection involves an amplification as well. Northern blots, dot blots, microarrays, quantitative PCR and quantitative RT-PCR are all well known methods for detecting a nucleic acid in a sample.

In certain embodiments, the invention provides nucleic acid probes that bind specifically to a 15-PGDH nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

A variety of methods of specific DNA and RNA measurement that use nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a 15-PGDH polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.,* 63:378-383 (1969); and John et al. *Nature,* 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immuoassays,*" *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies that can serve as specific binding pair members for a labeled ligand. An introduction to labels, labeling procedures and detection of labels is found in Polak and Van Noorden, *Introduction to Immunocytochemistry,* 2nd ed., Springer Verlag, NY (1997); and in Haugland, *Handbook of Fluorescent Probes and Research Chemicals*, a combined handbook and catalogue Published by Molecular Probes, Inc. (1996).

In general, a detector that monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

The amount of, for example, an RNA is measured by quantifying the amount of label fixed to the solid support by binding of the detection reagent. Typically, the presence of a modulator during incubation will increase or decrease the amount of label fixed to the solid support relative to a control incubation that does not comprise the modulator, or as compared to a baseline established for a particular reaction type. Means of detecting and quantitating labels are well known to those of skill in the art.

In some embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), i.e. Gene Chips or microarrays, available from Affymetrix, Inc. in Santa Clara, Calif. can be used to detect changes in expression levels of a plurality of genes involved in the same regulatory pathways simultaneously. See, Tijssen, supra., Fodor et al. (1991) *Science,* 251: 767-777; Sheldon et al. (1993) *Clinical Chemistry* 39(4): 718-719, and Kozal et al. (1996) *Nature Medicine* 2(7): 753-759. Similarly, spotted cDNA arrays (arrays of cDNA sequences bound to nylon, glass or another solid support) can also be used to monitor expression of a plurality of genes.

Typically, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment. See, e.g., Schena et al., *Science* 270: 467-470 (1995) and Lockhart et al., *Nature Biotech.* 14: 1675-1680 (1996). The various methods of evaluating hybridization detection and specificity are described in US 2006160076 A1, incorporated herein in its entirety.

Detection of nucleic acids can also be accomplished, for example, by using a labeled detection moiety that binds specifically to duplex nucleic acids (e.g., an antibody that is specific for RNA-DNA duplexes). One example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181: 153-162; Bogulayski (1986) et al. *J. Immunol. Methods* 89:123-130; Prooijen-Knegt (1982) *Exp. Cell Res.* 141:397-407; Rudkin (1976) *Nature* 265:472-473, Stollar (1970) *PNAS* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (ed) *Fundamental Immunology, Third Edition* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1989); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman and molecular beacon probes can be used to monitor amplification reaction products, e.g., in real time.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

Single nucleotide polymorphism (SNP) analysis is also useful for detecting differences between alleles of 15-PGDH genes. 15-PGDH linked SNPs are useful, for instance, for diagnosis of 15-PGDH-linked diseases (e.g., colon cancer) in a patient. For example, if an individual carries at least one allele of a 15-PGDH-linked SNP, the individual is likely predisposed for one or more of those diseases. If the individual is homozygous for a disease-linked 15-PGDH SNP, the individual is particularly predisposed for 15-PGDH-linked disease. In some embodiments, the SNP associated with the 15-PGDH-linked disease is located within 300,000; 200,000; 100,000; 75,000; 50,000; or 10,000 base pairs of a polynucleotide encoding 15-PGDH.

Various real-time PCR methods including, e.g., Taqman or molecular beacon-based assays (e.g., U.S. Pat. Nos. 5,210, 015; 5,487,972; Tyagi et al., (1996) *Nature Biotechnology* 14:303; and PCT WO 95/13399) are useful to monitor for the presence of absence of a SNP. Additional SNP detection methods include, e.g., DNA sequencing, sequencing by hybridization, dot blotting, oligonucleotide array (DNA Chip) hybridization analysis, or are described in, e.g., U.S. Pat. No. 6,177,249; Landegren et al., (1998) *Genome Research*, 8:769-776; Botstein et al., (1980) *Am J Human Genetics* 32:314-331; Meyers et al., (1987) *Methods in Enzymology* 155:501-527; Keen et al., (1991) *Trends in Genetics* 7:5; Myers et al., (1985) *Science* 230:1242-1246; and Kwok et al., (1994) *Genomics* 23:138-144.

Immunological Measurement/Detection of 15-PGDH

In certain embodiments, a method of the invention comprises detecting the levels of the 15-PGDH protein in a sample. Additionally, a method of the invention comprises detecting the activity level of 15-PGDH (e.g., an assay which measures the enzymatic activity of 15-PGDH, as known in the art). Optionally, the method involves obtaining a quantitative measure of the 15-PGDH protein in the sample. In view of this specification, one of skill in the art will recognize a wide range of techniques that may be employed to detect and optionally quantify the presence of a protein. A general overview of the applicable technology can be found in Harlow & Lane, *Antibodies: A Laboratory Manual* (1988). In some embodiments, the 15-PGDH protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots.

Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein Nature, 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the 15-PGDH sequence is conjugated to a carrier protein and used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their crossreactivity against non-15-PGDH proteins or even other homologous proteins from other organisms, using a competitive binding immunoassay. Specific monoclonal and polyclonal antibodies and antisera will usually bind with a $K_D$ of at least about 0.1 mM, more usually at least about 1 µM, preferably at least about 0.1 µM or better, and most preferably, 0.01 µM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to 15-PGDH. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, Eur. J. Immunol. 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a binding fragment thereof by screening a DNA library from human B cells according to the general protocol outlined by Huse et al., supra.

Once target immunogen-specific antibodies are available, the immunogen can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio Enzyme Immunoassay, CRC Press, Boca Raton, Fla. (1980); Tijssen, supra; and Harlow and Lane, supra.

Immunoassays to measure target proteins in a human sample may use a polyclonal antiserum that was raised to the protein (e.g., 15-PGDH) or a fragment thereof. This antiserum is selected to have low cross-reactivity against non-15-PGDH proteins and any such cross-reactivity is removed by immunoabsorption prior to use in the immunoassay.

In some embodiments, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai Methods in Cell Biology Volume 37: Antibodies in Cell Biology, Academic Press, Inc. NY (1993); Stites, supra. Immunological binding assays (or immunoassays) typically utilize a "capture agent" to specifically bind to and often immobilize the analyte (in this case 15-PGDH of the present invention, or antigenic subsequences thereof). The capture agent is a moiety that specifically binds to the analyte. In a preferred embodiment, the capture agent is an antibody that specifically binds, for example, a 15-PGDH polypeptide of the invention. The antibody (e.g., anti-15-PGDH antibody) may be produced by any of a number of means well known to those of skill in the art and as described above.

Immunoassays also often utilize a labeling agent to bind specifically to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J Immunol.*, 111: 1401-1406 (1973); and Akerstrom, et al. *J Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

Immunoassays for detecting proteins or analytes of interest from tissue samples may be either competitive or noncompetitive. Noncompetitive immunoassays are assays in which the amount of captured protein or analyte is directly measured. In one preferred "sandwich" assay, for example, the capture agent (e.g. 15-PGDH antibodies) can be bound directly to a solid substrate where it is immobilized. These immobilized antibodies then capture the 15-PGDH present in the test sample. The 15-PGDH thus immobilized is then bound by a labeling agent, such as a second anti-15-PGDH antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

In competitive assays, the amount of protein or analyte present in the sample is measured indirectly by measuring the amount of an added (exogenous) protein or analyte (e.g., the 15-PGDH of interest) displaced (or competed away) from a specific capture agent (e.g., antibodies raised to 15-PGDH) by the protein or analyte present in the sample. The amount of immunogen bound to the antibody is inversely proportional to the concentration of immunogen present in the sample. In a particularly preferred embodiment, the antibody is immobilized on a solid substrate. The amount of analyte may be detected by providing a labeled analyte molecule. It is understood that labels can include, e.g., radioactive labels as well as peptide or other tags that can be recognized by detection reagents such as antibodies.

Immunoassays in the competitive binding format can be used for cross-reactivity determinations. For example, the protein encoded by the sequences described herein can be immobilized on a solid support. Proteins are added to the assay and compete with the binding of the antisera to the immobilized antigen. The ability of the above proteins to compete with the binding of the antisera to the immobilized protein is compared to that of the protein encoded by any of the sequences described herein. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

In other embodiments, western blot (immunoblot) analysis is used to detect and quantify the presence of a 15-PGDH in the sample. The technique generally comprises separating sample proteins by gel electrophoresis on the basis of molecular weight, transferring the separated proteins to a suitable solid support (e.g., a nitrocellulose filter, a nylon filter, or a derivatized nylon filter) and incubating the sample with the antibodies that specifically bind the protein of interest. For example, the anti-15-PGDH antibodies specifically bind to the 15-PGDH on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:3441).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

Identification of Modulators of 15-PGDH

Modulators of 15-PGDH, i.e. agonists or antagonists of 15-PGDH activity, or 15-PGDH polypeptide or polynucleotide expression, are useful for treating a number of human diseases, including cancer. For example, administration of 15-PGDH upregulators can be used to treat patients with colon neoplasia, e.g., colon cancer or colon adenoma, or patients with a history of colon neoplasia with resistance to NSAID therapy for neoplasia therapy or neoplasia preventive therapy. Further, administration of 15-PGDH upregulators can be used to treat subjects having an NSAID-responsive condition, as described herein. In certain embodiments, 15-PGDH upregulators enhance NSAID-responsiveness in subjects who are relatively unresponsive to NSAID treatment.

Figure 4:
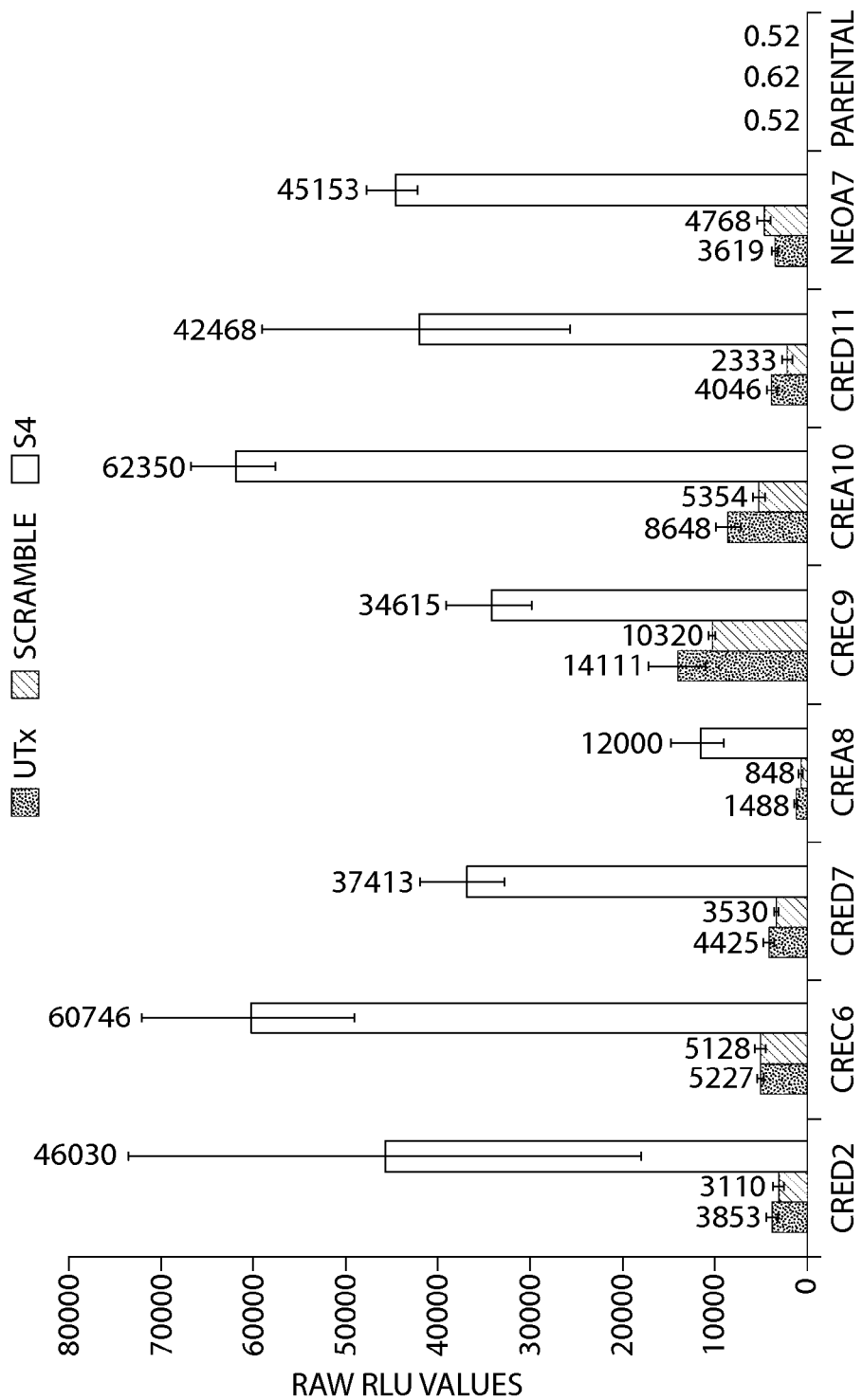
FIG. 4: Established colon cancer cell line for screening 15-PGDH modulators. By homologous recombination, a ranilla luciferase cassette was inserted in-frame into the silent PGDH locus in the LS-174 T cells. The figure illustrates the induction of the 15-PGDH-ranilla luciferase fusion protein as measured by luciferase activity upon treatment with a beta-catenin siRNA (denoted S4). Untransfected cells (UTX) and cells transfected with a control scrambled siRNA ("scramble") are also shown for comparison.

"Inhibitors," "activators," and "modulators" of 15-PGDH expression or of 15-PGDH activity are used to refer to inhibitory, activating, or modulating molecules, respectively, identified using in vitro and in vivo assays for 15-PGDH expression or 15-PGDH activity, e.g., ligands, agonists, antagonists, and their homologs and mimetics. The term "modulator" includes inhibitors and activators. Inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. Activators are agents that, e.g., induce or activate the expression of a 15-PGDH or bind to, stimulate, increase, open, activate, facilitate, or enhance activation, sensitize or up regulate the activity of 15-PGDH, e.g., agonists. Modulators include naturally occurring and synthetic ligands, small chemical molecules, and the like. Accordingly, a 15-PGDH activator may include an agent that enhances the activity or expression of 15-PGDH directly. In other embodiments, a 15-PGDH activator may include an agent that enhances the expression of 15-PGDH indirectly. For example, as described herein, turning off the beta-catenin transcription factor markedly induces the expression of both 15-PGDH mRNA and protein (FIG. 4).

Described herein are assays for identifying inhibitors and activators Such assays include, e.g., applying putative modulator compounds to cells expressing 15-PGDH and then determining the functional effects on 15-PGDH activity. Samples or assays comprising 15-PGDH that are treated with a potential activator, inhibitor, or modulator are compared to control samples without the inhibitor, activator, or modulator to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25, 10%, 5% or 1%. Activation of 15-PGDH is achieved when the 15-PGDH activity or expression value relative to the control is 105%, optionally 110%, optionally 125%, optionally 150%, optionally 200, 300%, 400%, 500%, or 1000-3000% or more higher.

Agents that Modulate 15-PGDH

The agents tested as modulators of 15-PGDH can be any small chemical compound, or a biological entity, such as a protein, sugar, nucleic acid or lipid. Typically, test compounds will be small chemical molecules and peptides. Essentially any chemical compound can be used as a potential modulator or ligand in the assays of the invention. The assays are designed to screen large chemical libraries by automating the assay steps and providing compounds from any convenient source to assays, which are typically run in parallel (e.g., in microtiter formats on microtiter plates in robotic assays). Modulators also include agents designed to increase the level of 15-PGDH mRNA or the level of translation from an mRNA. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Some examples of small molecules that induce 15-PGDH mRNA levels include, but are not limited to, erlotinib (Backlund, M. G. et al., (2005) *J Biol Chem* 280, 3217-23), butyrate (Backlund, M. G., et al, (2008) *Cancer Res* 68(22), 9331-9337) and Prox-1 suppressors (U.S. Patent Publication No. 2007/0026405).

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g. Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

In other embodiments, agents that modulate 15-PGDH levels include antisense molecules, ribozymes, DNAzymes, small inhibitory RNAs and the like that act on other proteins, the silencing of which causes an induction in 15-PGDH levels (e.g., silencing of beta-catenin transcription factor).

Methods of Screening for Modulators of 15-PGDH

A number of different screening protocols can be utilized to identify agents that modulate the level of expression or activity of 15-PGDH in cells, particularly mammalian cells, and especially human cells. In general terms, the screening methods involve screening a plurality of agents to identify an agent that modulates the activity of 15-PGDH by, e.g., binding to a 15-PGDH polypeptide, preventing an inhibitor or activator from binding to 15-PGDH, increasing association of an inhibitor or activator with 15-PGDH, or activating expression of 15-PGDH.

Any cell expressing 15-PGDH or a fragment thereof can be used to identify modulators. In some embodiments, the cells are eukaryotic cells lines (e.g., CHO or HEK293) transformed to express a heterologous 15-PGDH polypeptide. In some embodiments, a cell expressing an endogenous 15-PGDH is used in screens. In other embodiments, modulators are screened for their ability to effect the levels of $PGE_2$.

Binding Assays

Preliminary screens can be conducted by screening for agents capable of binding to 15-PGDH, as at least some of the agents so identified are likely 15-PGDH modulators. Binding assays are also useful, e.g., for identifying endogenous proteins that interact with 15-PGDH. For example, antibodies, receptors or other molecules that bind 15-PGDH can be identified in binding assays.

Binding assays usually involve contacting a 15-PGDH protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to 15-PGDH or displacement of labeled substrates. The 15-PGDH proteins utilized in such assays can be naturally expressed, cloned or synthesized.

In addition, mammalian or yeast two-hybrid approaches (see, e.g., Bartel, P. L. et. al. *Methods Enzymol*, 254:241 (1995)) can be used to identify polypeptides or other molecules that interact or bind when expressed together in a host cell.

Expression Assays

Screening for a compound that modulates the expression of 15-PGDH are also provided. Screening methods generally involve conducting cell-based assays in which test compounds are contacted with one or more cells expressing 15-PGDH, and then detecting an increase or decrease in 15-PGDH expression (either transcript or translation product). Assays can be performed with any cells that express 15-PGDH.

15-PGDH expression can be detected in a number of different ways. As described infra, the expression level of 15-PGDH in a cell can be determined by probing the mRNA expressed in a cell with a probe that specifically hybridizes with a transcript (or complementary nucleic acid derived therefrom) of 15-PGDH. Probing can be conducted by lysing the cells and conducting Northern blots or without lysing the cells using in situ-hybridization techniques. Alternatively, 15-PGDH protein can be detected using immunological methods in which a cell lysate is probed with antibodies that specifically bind to 15-PGDH.

Other cell-based assays involve reporter assays conducted with cells using standard reporter gene assays. These assays can be performed in either cells that do, or do not, express 15-PGDH. Some of these assays are conducted with a heterologous nucleic acid construct that includes a 15-PGDH promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector, or a ranilla luciferase (see FIG. 4 and Example 4). Other reporters generate a detectable product. Often such reporters are enzymes. Exemplary enzyme reporters include, but are not limited to, β-glucuronidase, CAT (chloramphenicol acetyl transferase; Alton and Vapnek (1979) *Nature* 282: 864-869), luciferase, β-galactosidase and alkaline phosphatase (Toh, et al. (1980) *Eur. J. Biochem.* 182:231-238; and Hall et al. (1983) *J. Mol. Appl. Gen.* 2: 101).

In these assays, cells harboring the reporter construct are contacted with a test compound. Modulated promoter expression is monitored by detecting the level of a detectable reporter. A number of different kinds of 15-PGDH modulators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of 15-PGDH expression levels for a control population (e.g., healthy individuals as described herein) or cells (e.g., tissue culture cells not exposed to a 15-PGDH modulator). Expression levels can also be determined for cells that do not express 15-PGDH as a negative control.

A variety of different types of cells can be utilized in the reporter assays. Cells that express an endogenous 15-PGDH include, e.g., monocytes, neutrophils, leukocytes or brain, spleen cells, skeletal muscle or adipocytes. Cells that do not endogenously express 15-PGDH can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the HEK293, HepG2, COS, CHO and HeLa cell lines, as well as established cancer cell lines, e.g., colon cancer cell lines.

Various controls can be conducted to ensure that an observed activity is authentic including running parallel reactions with cells that lack the reporter construct or by not contacting a cell harboring the reporter construct with test compound. Compounds can also be further validated as described below.

In a preferred embodiment proteins described herein are used in drug screening assays. The proteins, antibodies, nucleic acids, modified proteins and cells are used in drug screening assays or by evaluating the effect of drug candidates on a "gene expression profile" or expression profile of polypeptides. In a preferred embodiment, the expression profiles are used, preferably in conjunction with high throughput screening techniques to allow monitoring for expression profile genes after treatment with a candidate agent (e.g., Zlokarnik, et al., *Science* 279:84-8 (1998); Heid, Genome Res 6:986-94, 1996).

In a preferred embodiment, the proteins, antibodies, nucleic acids, modified proteins and cells containing the native or modified proteins are used in screening assays. That is, the present invention provides methods for screening for compositions which modulate the protein or mRNA levels of 15-PGDH or an identified physiological function of the 15-PGDH protein. This can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Expression monitoring can be performed to identify compounds that modify the expression of 15-PGDH. Generally, in a preferred embodiment, a test compound is added to the cells prior to analysis. Moreover, screens are also provided to identify agents that modulate the growth of or prevent colorectal cancer, modulate 15-PGDH, bind to 15-PGDH, or interfere with the binding of a 15-PGDH protein and an antibody, substrate, or other binding partner.

Compositions, Kits and Integrated Systems

The invention provides compositions, kits and integrated systems for practicing the assays described herein using nucleic acids encoding the 15-PGDH polypeptides of the invention, or 15-PGDH proteins, anti-15-PGDH antibodies, etc.

The invention provides assay compositions for use in solid phase assays; such compositions can include, for example, one or more nucleic acids encoding a 15-PGDH immobilized on a solid support, and a labeling reagent. In each case, the assay compositions can also include additional reagents that are desirable for hybridization. Modulators of expression or activity of a 15-PGDH of the invention can also be included in the assay compositions.

The invention also provides kits for carrying out the assays of the invention. The kits typically include a probe that comprises an antibody that specifically binds to 15-PGDH or a polynucleotide sequence encoding a 15-PGDH polypeptide, and a label for detecting the presence of the probe. The kits may include at least one polynucleotide sequence encoding a 15-PGDH polypeptides of the invention. Kits can include any of the compositions noted above, and optionally further include additional components such as instructions to practice a high-throughput method of assaying for an effect on expression of the genes encoding the 15-PGDH polypeptides of the invention, or on activity of the 15-PGDH polypeptides of the invention, one or more containers or compartments (e.g., to hold the probe, labels, or the like), a control modulator of the expression or activity of 15-PGDH polypeptides, a robotic armature for mixing kit components or the like.

The invention also provides integrated systems for high-throughput screening of potential modulators for an effect on the expression or activity of the 15-PGDH polypeptides of the invention. The systems can include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous binding assays.

Optical images viewed (and, optionally, recorded) by a camera or another recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, 052® WINDOWS®, WINDOWS NT®, WINDOWS95®, WINDOWS98®, or WINDOWS2000' based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Administration and Pharmaceutical Compositions

Modulators of 15-PGDH can be administered directly to the mammalian subject for modulation of 15-PGDH levels and/or activity in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the 15-PGDH, alone or in combination with other suitable components (e.g., an NSAID), can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, 15-PGDH modulators of the present invention can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents (e.g., an NSAID) depending on the desired target therapy. Combination therapy includes administration of a single pharmaceutical dosage formulation that contains a 15-PGDH modulator of the invention and one or more additional active agents, as well as administration of a 15-PGDH modulator and each active agent in its own separate pharmaceutical dosage formulation. For example, a 15-PGDH modulator and celecoxib can be administered to the human subject together in a single oral dosage composition, such as a tablet or capsule, or each agent can be administered in separate oral dosage formulations. In other embodiments, an NSAID, e.g., celecoxib or aspirin, may be administered with an effective amount of the 15-PGDH protein. Where separate dosage formulations are used, an 15-PGDH modulator and one or more additional active agents can be administered at essentially the same time (i.e., concurrently), or at separately staggered times (i.e., sequentially). Combination therapy is understood to include all these regimens.

Gene Therapy

Conventional viral and non-viral based gene transfer methods can be used to introduce nucleic acids encoding engineered polypeptides of 15-PGDH in mammalian cells or target tissues. Such methods can be used to administer nucleic acids encoding polypeptides of the invention (e.g., 15-PGDH, including variants thereof) to cells in vitro. In some embodiments, the nucleic acids encoding polypeptides of the invention are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11: 162-166 (1993); Dillon, *TIBTECH* 11:167-175 (1993); Miller, *Nature* 357:455-460 (1992); Van Brunt, *Biotechnology* 6(10): 1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds) (1995); and Yu et al., *Gene Therapy* 1:13-26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787, and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered polypeptides of the invention take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof (see, e.g. Buchscher et al., *J. Virol.* 66, 2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the polypeptides of the invention is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251-3260 (1985); Tratschin, et al.; *Mol. Cell. Biol.* 4:2072-2081 (1984); Hermonat & Muzyczka, *PNAS* 81:6466-6470 (1984); and Samulski et al., *J. Virol.* 63:03822-3828 (1989).

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:15-10 (1996); Sterman et al., *Hum. Gene Ther.* 9:7 1083-1089 (1998); Welsh et al., *Hum. Gene Then.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA) encoding a polypeptides of the invention, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

15-PGDH Nucleic Acid and their Uses

Nucleic acids disclosed herein may be used in several ways. In a first embodiment, nucleic acid probes are made and attached to biochips to be used in screening and diagnostic methods, as outlined below, or for administration, e.g., for gene therapy, and/or antisense applications. Alternatively, nucleic acids that include coding regions of 15-PGDH can be put into expression vectors for the expression of the proteins, again for screening purposes or for administration to a subject. Two isoforms of 15-PGDH are known: 1) NM_000860.4 corresponding to NP_000851.2 (isoform 1) and 2) NM_001145816.1 corresponding to NP_001139288.1 (isoform 2). Isoform 2 lacks exon 6 and, therefore, corresponds to a catalytically dead variant. For any of the diagnostic and screening methods described herein, the levels of either isoform can be detected and/or measured.

In a preferred embodiment, nucleic acid probes to a nucleic acid disclosed herein (both the nucleic acid sequences outlined in the figures and/or the complements thereof) are made. The nucleic acid probes attached to the biochip are designed to be substantially complementary to 15-PGDH nucleic acids, i.e. the target sequence (either the target sequence of the sample or to other probe sequences, e.g., in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under appropriate reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally complements of ORFs or whole genes are not used. In some embodiments, nucleic acids of lengths up to hundreds of bases can be used.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e., have some sequence in common), or separate. In some cases, PCR primers may be used to amplify signal for higher sensitivity.

15-PGDH nucleic acids may be used to make a variety of expression vectors to express proteins which can then be used in screening assays or to generate antibodies, as described herein. Expression vectors and recombinant DNA technology are well known to those of skill in the art (see, e.g., Ausubel, supra, and Gene Expression Systems (Fernandez & Hoeffler, eds, 1999)) and are used to express proteins. The expression vectors may be either self-replicating extrachromosomal vectors or vectors which integrate into a host genome. Generally, these expression vectors include transcriptional and translational regulatory nucleic acid operably linked to the nucleic acid encoding the metastatic colorectal cancer protein.

The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers. Transcriptional and translational regulatory nucleic acid will generally be appropriate to the host cell used to express the protein. Numerous types of appropriate expression vectors, and suitable regulatory sequences are known in the art for a variety of host cells. In general, transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences. Promoter sequences encode either constitutive or inducible promoters. The promoters may be either naturally occurring promoters or hybrid promoters. Hybrid promoters, which combine elements of more than one promoter, are also known in the art, and are useful in the present invention. In addition, an expression vector may comprise additional elements. For example, the expression vector may have two replication systems, thus allowing it to be maintained in two organisms, e.g., in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art. In addition, in a preferred embodiment, the expression vector contains a selectable marker gene to allow the selection of transformed host cells. Selection genes are well known in the art and will vary with the host cell used.

The 15-PGDH protein disclosed herein may be produced by culturing a host cell transformed with an expression vector containing a nucleic acid encoding 15-PGDH, or functional fragments/variants thereof, under the appropriate conditions to induce or cause expression of the metastatic colorectal cancer protein. Conditions appropriate for protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield. Appropriate host cells include yeast, bacteria, archaebacteria, fungi, and insect and animal cells, including mammalian cells. Of particular interest are *Saccharomyces cerevisiae* and other yeasts, *E. coli*, Bacillus subtilis, Sf9 cells, C129 cells, 293 cells, *Neurospora*, BHK, CHO, COS, HeLa cells, HLVEC (human umbilical vein endothelial cells), THP1 cells (a macrophage cell line) and various other human cells and cell lines.

In one embodiment, the proteins are derivative or variant 15-PGDH proteins as compared to the wild-type sequence. That is, as outlined more fully below, the derivative peptide will often contain at least one amino acid substitution, deletion or insertion, with amino acid substitutions being particularly preferred. The amino acid substitution, insertion or deletion may occur at a particular residue within the peptide. Also included within one embodiment of 15-PGDH proteins of the present invention are amino acid sequence variants. These variants typically fall into one or more of three classes: substitutional, insertional or deletional variants. These variants ordinarily are prepared by site specific mutagenesis of nucleotides in the encoding DNA, using cassette or PCR mutagenesis or other techniques, to produce DNA encoding the variant, and thereafter expressing the DNA in recombinant cell culture as outlined above. However, variant protein fragments having up to about 100-250 residues may be prepared by in vitro synthesis. Amino acid sequence variants are characterized by the predetermined nature of the variation, a feature that sets them apart from naturally occurring allelic or inter-species variation of the metastatic colorectal cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is often predetermined, the mutation per se need not be predetermined. For example, in order to optimize the performance of a mutation at a given site, random mutagenesis may be conducted at the target codon or region and the expressed variants screened for the optimal combination of desired activity. Techniques exist for making substitution mutations at predetermined sites in DNA having a known sequence, e.g., M13 primer mutagenesis and PCR mutagenesis. Screening of the mutants is done using assays of protein activities.

Amino acid substitutions are typically of single residues; insertions usually will be on the order of from about 1 to 20 amino acids, although considerably larger insertions may be occasionally tolerated. Deletions range from about 1 to about 20 residues, although in some cases deletions may be much larger.

Substitutions, deletions, truncations, insertions or any combination thereof may be used to arrive at a final derivative. Generally these changes are done on a few amino acids to minimize the alteration of the molecule. Larger changes may be tolerated in certain circumstances. When small alterations in the characteristics of a protein are desired, substitutions are generally made in accordance with the amino acid substitution commonly known in the art.

Variants typically exhibit the same qualitative biological activity and will elicit the same immune response as the naturally-occurring analog, although variants also are selected to modify the characteristics of the metastatic colorectal cancer proteins as needed. Alternatively, the variant may be designed or reorganized such that the biological activity of the is altered. For example, glycosylation sites may be altered or removed. When a 15-PGDH protein is to be used to generate antibodies, e.g., for immunotherapy or immunodiagnosis, the protein should share at least one epitope or determinant with the full length protein. By "epitope" or "determinant" herein is typically meant a portion of a protein which will generate and/or bind an antibody or T-cell receptor in the context of MHC. Thus, in most instances, antibodies made to a smaller metastatic colorectal cancer protein will be able to bind to the full-length protein, particularly linear epitopes. In a preferred embodiment, the epitope is unique; that is, antibodies generated to a unique epitope show little or no cross-reactivity. Methods of preparing polyclonal or monoclonal antibodies are well known in the art (e.g., Coligan, supra; and Harlow & Lane, supra; Kohler & Milstein, Nature 256:495 (1975)).

EXEMPLIFICATION

The invention now being generally described, it will be more readily understood by reference to the following examples, which are included merely for purposes of illustration of certain aspects and embodiments of the present invention, and are not intended to limit the invention. Although exemplification is provided in the context of colon cancer, one of skill in the art would readily appreciate the applicability of the invention to other forms of cancer.

Example 1

15-PGDH is Required for Celecoxib Prevention of Murine Colon Tumors

Figure 1B:
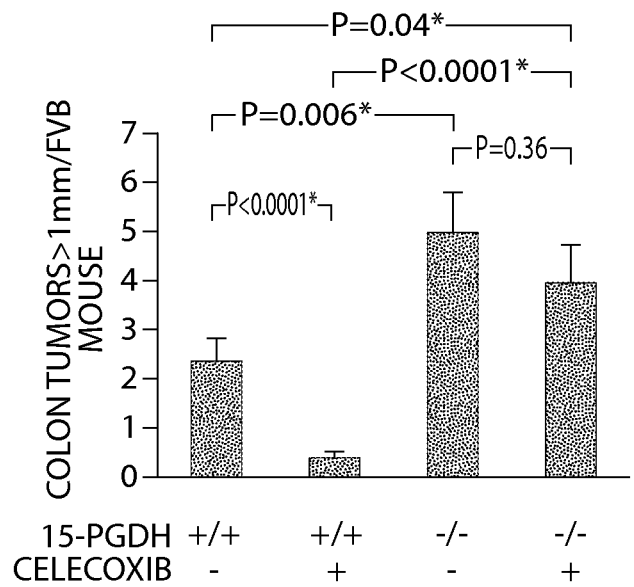
Figure 1C:
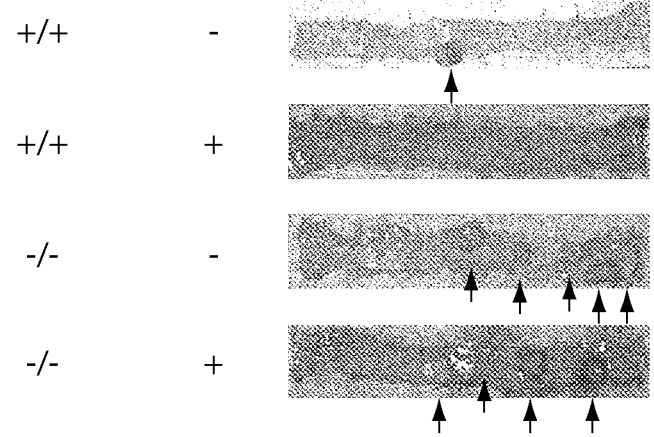

To conduct this study FVB mice were selected, chosen because at baseline this mouse strain is sensitive to AOM induced colon tumors (Nambiar, P. R. et al., (2003) *Int Oncol* 22, 145-50). In 15-PGDH wild-type FVB mice, AOM induced 2.3±0.4 tumors per mouse colon (FIG. 1A, 1C), which on histology review were all adenomatous lesions. As in human trials, administering dietary celecoxib protected wild-type FVB mice against colon tumor development, reducing adenoma development to 0.7±0.3 tumors per mouse (P=0.003) (FIG. 1A, 1C). Furthermore, while nearly all tumors arising in control mice exceeded 1 mm in size, tumors in celecoxib treated mice rarely reached this size (2.2±0.4 versus 0.3±0.1, P<0.0001) (FIG. 1B).

Dietary celecoxib could thus near completely protect wild-type FVB mice from developing colon tumors. Further investigation however revealed that the ability of celecoxib to protect mice from colon tumors was crucially dependent upon the concomitant activity of 15-PGDH, and that this protection could be abrogated by breeding 15-PGDH knock-out alleles into the FVB strain. Thus, celecoxib treated 15-PGDH null mice developed 5.5-fold more colon adenomas than did their celecoxib treated 15-PGDH wild-type littermates (3.9±0.8 versus 0.7±0.3, P=0.0001) (FIG. 1A, 1C). Moreover, all colonic adenomas arising in celecoxib treated knockout mice were large, each exceeding 1 mm in size; whereas, large tumors were nearly completely absent in celecoxib treated 15-PGDH wild-type mice (3.9±0.8 large tumors per knockout mouse versus 0.3±0.1 per wild-type, P=0.0001) (FIG. 1B, 1C). By several measures, 15-PGDH knockout mice were almost completely resistant to the colon tumor prevention effects of celecoxib. For example, tumor development in the knockout mice did not significantly differ between celecoxib treated versus untreated animals (3.9±0.8 versus 4.9±0.8, respectively, P=0.36) (FIG. 1A). Moreover, colon tumor development in celecoxib treated 15-PGDH knockout mice actually exceeded that of drug untreated wild-type mice (3.9±0.8 versus 2.2±0.4 respectively, for tumors>1 mm in size, P=0.04; and, 3.9±0.8 versus 2.3±0.4 respectively tumors of any size, P=0.06) (FIG. 1A, 1B). We conclude that celecoxib mediated colon tumor prevention requires concurrent presence of the prostaglandin inactivating activity of colonic 15-PGDH, and that 15-PGDH loss confers in vivo resistance to this drug effect.

Example 2

15-PGDH is Required for Celecoxib Reduction of Colonic $PGE_2$

Figure 1D:
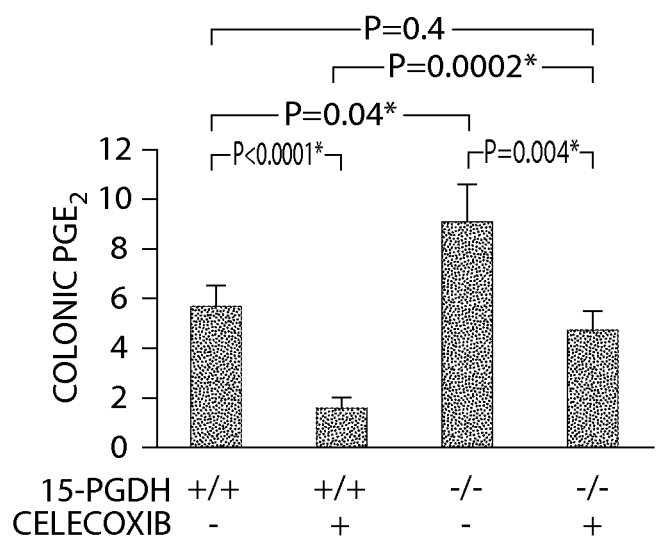
Figure 2:
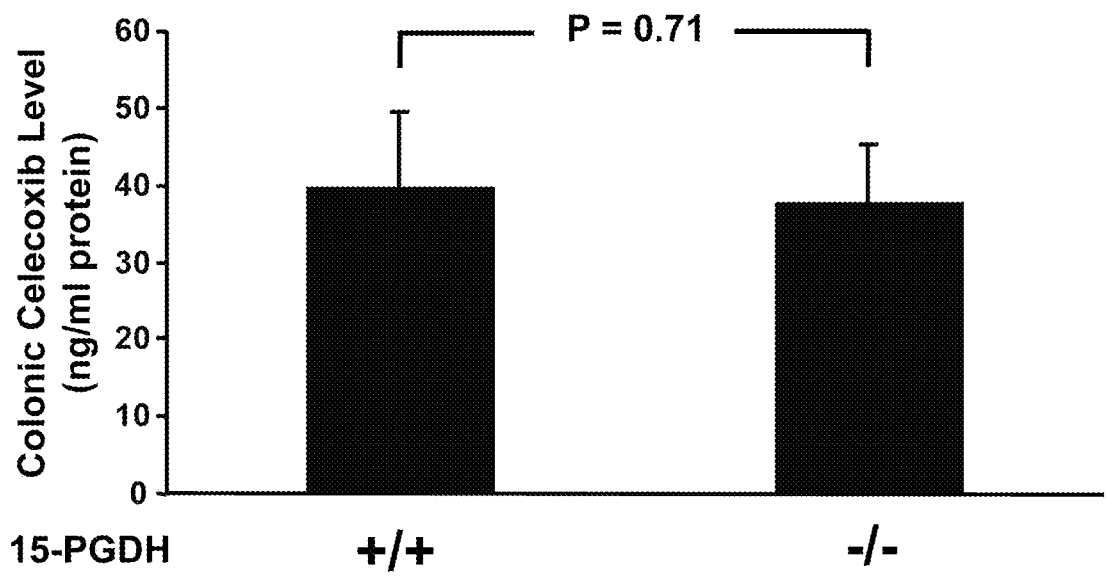
FIG. 2: Celecoxib and 15-PGDH tissue levels in murine colonic mucosa. (A) Tissue levels of celecoxib were determined by mass spectrometry in tissue homogenates of colonic mucosa obtained from 15-PGDH wild-type (+/+) (n=20) or knockout (−/−) (n=26) mice administered two weeks of a celecoxib supplemented diet. Error bars designate standard error of the mean. Mice cohorts correspond to those of FIG. 1D. (B) Western analysis of 15-PGDH expression determined in colon mucosa from 3 sets of mice receiving two weeks of a control (−) or two weeks of a celecoxib-containing (+) diet. Actin protein levels serve as a loading control.
Figure 2:
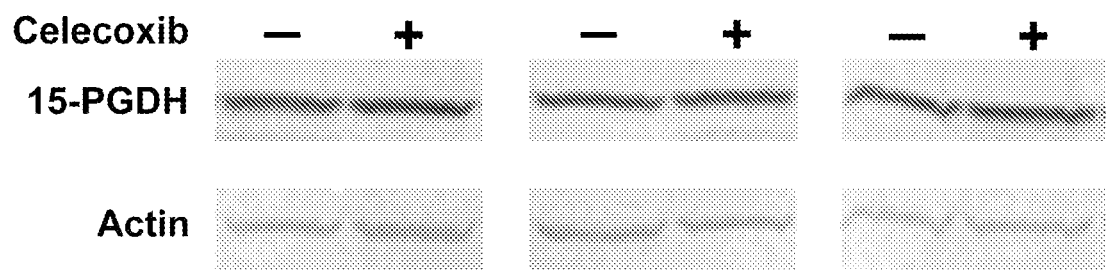

To further investigate the mechanism of celecoxib's dependence on 15-PGDH, we determined $PGE_2$ levels in colonic mucosa of FVB mice under different experimental conditions. Consistent with the role of 15-PGDH in mediating prostaglandin degradation, 15-PGDH gene knockout essentially doubled FVB colonic $PGE_2$ levels (9.1±1.5 ng/mg protein in knockouts versus 5.70±0.8 ng/mg protein in controls, P=0.04) (FIG. 1D). Celecoxib treatment of 15-PGDH wild-type mice markedly lowered $PGE_2$ levels to 1.6±0.4 ng/mg protein (P<0.001) (FIG. 1D). In contrast, in 15-PGDH knockout mice the biochemical activity of celecoxib was much attenuated, with the drug lowering $PGE_2$ levels to only 4.7±0.8 ng/mg protein. This level was three-fold the level achieved in drug treated wild-type mice (P=0.0002), and was not significantly different from the $PGE_2$ level of drug free wild-type mice (P=0.4) (FIG. 1D). In overview, the efficacy of celecoxib in lowering colonic $PGE_2$ levels in these different models closely paralleled the drug's anti-tumor activity (FIG. 1D versus FIG. 1A, 1B), and mice that lacked 15-PGDH equally acquired resistance to celecoxib's biochemical activity of lowering colonic $PGE_2$ and to celecoxib's phenotypic effect of preventing colon tumors. Celecoxib resistance of 15-PGDH null mice was not due to any change in drug absorption or catabolism, as tissue levels of celecoxib were indistinguishable between drug treated 15-PGDH wild-type and null mice (39.5±9.7 versus 37.7±7.6 ng/mg protein, P=0.7) (FIG. 2A). Additionally, celecoxib did not regulate 15-PGDH levels, as Western blot analysis showed equal colonic 15-PGDH amounts in celecoxib treated versus untreated wild-type mice (FIG. 2B). Rather, the effective depletion of colonic $PGE_2$ required the COX-2 inhibitor drug to act in concert with the independent prostaglandin degrading activity of 15-PGDH.

Example 3

Figure 3:
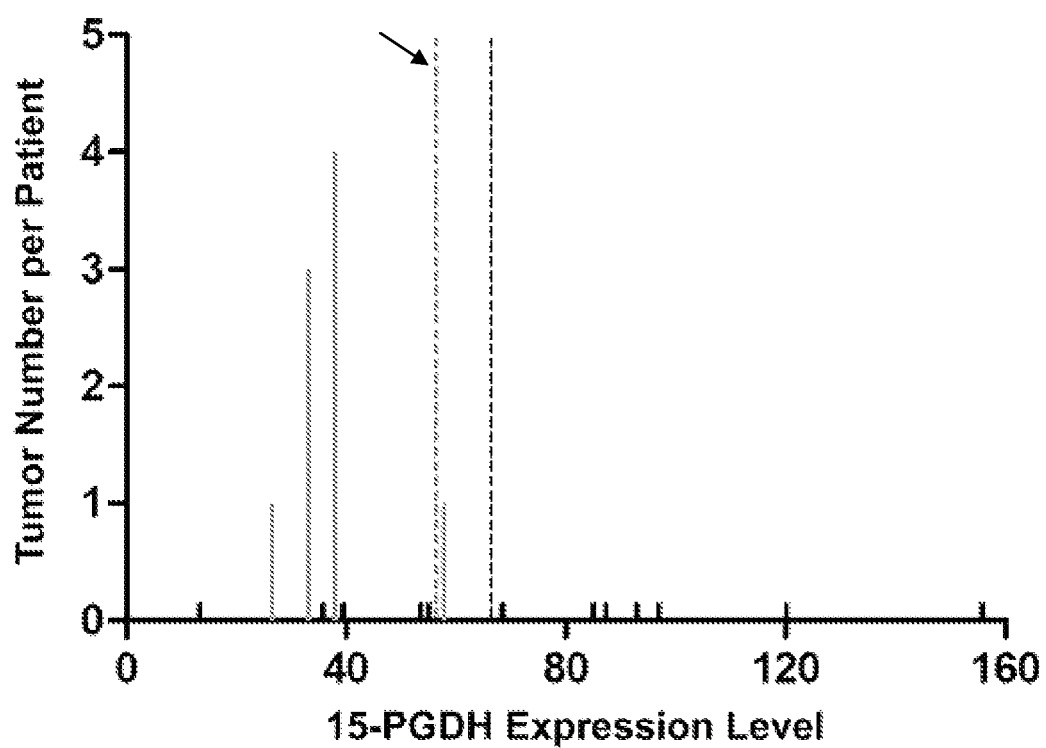
FIG. 3: Celecoxib resistance in humans with low levels of 15-PGDH. Shown on the X-axis are pre-treatment 15-PGDH transcript levels measured by real-time PCR in RNA from rectal mucosal biopsies of 16 individuals enrolled in the Adenoma Prevention with Celecoxib trial (Bertagnolli, M. M. et al, (2006) *N Engl J Med* 355, 873-84). Bar heights on the Y-axis indicate number of recurrent adenomas detected in each individual at the completion of 36 months of celecoxib treatment, with blue bars denoting individuals with recurrent disease, and with individuals with zero recurrences indicated by minimal black bars. Median level of 15-PGDH is denoted by the dashed line (and indicated by an arrow), and the mean level is denoted by the dashed line (not indicated by arrow).

Low 15-PGDH Levels are Associated with Celecoxib Resistance in Humans with Recurrent Colon Adenomas These observations in mice suggest that humans with lower levels of colonic 15-PGDH might also be resistant to the colon tumor prevention activity of celecoxib. To test this hypothesis, we examined frozen biopsies of rectal mucosa obtained from 16 individuals at the time of their enrollment in the Adenoma Prevention with Celecoxib (APC) trial (Bertagnolli, M. M. et al., (2006) *N Engl J Med* 355, 873-84). These individuals were all at high risk for colon adenoma development based on having had multiple colon adenomas and/or adenomas greater than 5 mm in diameter prior to their enrollment. Following clearing of their colonic adenomas by colonoscopy, each individual received 36-months of daily treatment with celecoxib (Bertagnolli, M. M. et al., (2006) *N Engl J Med* 355, 873-84). Measurement by real-time PCR of 15-PGDH transcript levels in these pre-treatment biopsy samples showed a 12-fold variation from lowest to highest 15-PGDH mRNA level among these 16 unrelated individuals (median=56.4, mean=66.2, range: 13.3-155.7) (FIG. 3). Repeat colonoscopy after 36 months revealed that four of these individuals had proven resistant to celecoxib treatment, as evidenced by the development of new adenomas, that all arose at new locations (FIG. 3). In total 9 new adenomas were detected in these patients (FIG. 3). 15-PGDH levels among individuals who developed new adenomas were lower than 15-PGDH levels among individuals who remained adenoma free (P=0.04) (FIG. 3). This can be further appreciated by noting that all four individuals with new adenomas demonstrated 15-PGDH levels below the cohort mean (P=0.03) (FIG. 3). The relationship of low 15-PGDH level to celecoxib resistance becomes even stronger if analyzed in terms of the numbers of new adenomas that individuals developed, with 8 of the 9 adenomatous polyps that recurred during celecoxib treatment arising in individuals with colonic 15-PGDH values below the cohort median (P=0.01), and with all 9 new adenomas arising in individuals with colonic 15-PGDH below the cohort mean (P=0.001) (FIG. 3).

Accordingly, 15-PGDH activity can determine sensitivity or resistance to the colon tumor preventive activity of celecoxib. Gene knock-out of 15-PGDH confers near complete resistance to celecoxib colon tumor prevention in mice. More significantly, low levels of colonic 15-PGDH are associated with failure of celecoxib colon tumor prevention in man. These findings elucidate a previously unsuspected pharmacogenetic interaction that bears on the differences among different individuals in the efficacy of celecoxib treatment for prevention of colorectal adenomas. These observations show that measurement of 15-PGDH is clinically useful in selecting patients most likely to benefit from treatment with COX-2 inhibitors for colon tumor chemoprevention. Further, these observations also demonstrate the utility in identifying genetic markers to predict for individuals who are low expressers of 15-PGDH. In addition, these new observations further document the role of 15-PGDH as a key suppressor of tumor development in the colon. These results also show that agents capable of inducing or reactivating 15-PGDH expression provides new approaches for colon adenoma and cancer prevention, as well as colon cancer therapy.

Materials and Methods

Mouse Breeding

Mouse studies were conducted in the Case Animal Resource Center under a protocol approved by the Institutional Animal Care and Use Committee. 15-Hydroxyprostaglandin dehydrogenase (15-PGDH) knockout mice on a C57BL/6J background were generated as described previously (Myung, S. J. et al., (2006) Proc Natl Acad Sci USA 103, 12098-102; Coggins, K. G. et al, (2002) Nat Med 8, 91-2) and were bred to generation F8 onto an FVB/N (Jackson Laboratory, Bar Harbor, Me.) background, with genotyping done as previously described (Myung, S. J. et al., (2006) Proc Natl Acad Sci USA 103, 12098-102). 15-PGDH +/− mice generation F8 were intercrossed and siblings of 15-PGDH +/+ and −/− genotypes were selected out for studies with AOM and celecoxib. Eight- to 12-week-old mice were administered AOM by i.p. injection once weekly for 6 weeks at 10 mg/kg dose (Sigma Chemical Co., St. Louis, Mo.). Mice were euthanized 24 weeks after the last AOM injection. After euthanizing, the colons were opened longitudinally, rinsed with ice-cold PBS, and examined under a dissecting microscope to identify all tumors. Tumors were resected, fixed in 10% neutral buffered formalin, and paraffin-embedded for histologic examination. All mice received an AIN-76A diet (Harlan Teklad, Madison, Wis.). The diet of celecoxib treated mice was supplemented with 1250 mg/kg of this agent (LKT laboratories, St. Paul, Minn.) (Williams, C. S. et al., (2000) Cancer Res 60, 6045-51). In AOM studies, celecoxib supplementation was initiated starting the day of first AOM injection and continued throughout the lifetime of the mouse. In studies of colonic prostaglandin levels celecoxib was administered to a cohort of 8-12 week old mice continuously for 2 weeks, at which time mice were euthanized.

$PGE_2$ Analyses

Following 2 weeks of control or celecoxib supplemented diet mice were euthanized. The colons were opened and washed with ice cold PBS, and the colon mucosa was then gently scraped, snap frozen in liquid nitrogen and stored at −80° C. $PGE_2$ analyses were performed as previously described (Myung, S. J. et al., (2006) Proc Natl Acad Sci USA 103, 12098-102). To extract $PGE_2$ from mouse colon epithelial tissue, frozen mucosal samples (25-50 mg) were ground to a fine powder in a liquid-nitrogen-cooled mortar (Fisher Scientific). Samples were then transferred to sealed microcentrifuge tubes, and three times the volume of ice-cold PBS buffer containing 0.1% butylated hydroxytoluene (BHT) and 1 mM EDTA were added. The sample was then homogenized in an ultrasonic processor (Misonix, Farmingdale, N.J.) at 0° C. for 3 min. A 100-µl aliquot of the homogenate was transferred to a glass tube (13×100 mm) and subjected to extraction of eicosanoids by using a modified version of the method of Kempen et al. (Kempen, E. C. et al., (2001) Anal Biochem 297, 183-90). Briefly, 20-µl aliquots of 1 N citric acid and 10 µl of deuterated $PGE_2$ (100 ng/ml) were added to the samples. Eicosanoids were then extracted with 1 ml of hexane:ethyl acetate (1:1, vol/vol) and vortex-mixed for 2 min. Samples were centrifuged at 1,800×g for 10 min at 4° C. The upper organic layer was collected, and the organic phases from three extractions were pooled and then evaporated to dryness under a stream of nitrogen at room temperature. All extraction procedures were performed at minimum light levels under cold conditions (4° C.). Samples were then reconstituted in 100 µl of methanol:ammonium acetate buffer (10 mM, pH 8.5; 70:30, vol/vol) prior to liquid chromatography tandem MS (LC/MS/MS) analysis. The protein concentration was determined by a Bradford protein assay (Bio-Rad, Hercules, Calif.). $PGE_2$ was measured with reverse-phase LC electrospray ionization MS. LC/MS/MS analyses were performed with a Quattro Ultima tandem mass spectrometer (Micromass, Beverly, Mass.) equipped with an Agilent HP 1100 binary pump HPLC inlet. $PGE_2$ was separated by using a Luna 3µ Phenyl-Hexyl 2×150 mm LC column (Phenomenex, Torrance, Calif.). The mobile phase consisted of 10 mM ammonium acetate (pH 8.5) and methanol. The flow rate was 250 µl/min with a column temperature of 50° C. The sample injection volume was 25 µl. Samples were kept at 4° C. during the analysis. The mass spectrometer was operated in the electrospray negative-ion mode with a cone voltage of 100 V, a cone gas flow rate of 117 liters/h, and a devolution gas flow rate of 998 liters/h. The temperature of the desolvation region was 400° C., and the temperature of the source region was 120° C. Fragmentation for all compounds was performed by using argon as the collision gas at a collision cell pressure of $2.10 \times 10^{-3}$ torr. The collision energy was 19 V. Prostaglandins were detected by using electrospray negative ionization and multiple-reaction monitoring of the transition ions for the $PGE_2$ (351.2>271.2) and 13,14-dihydro-15-keto-$PGE_2$ (351.2>333.1). This method produces excellent linearity and a lower limit of quantitation of 10 ng/ml, which is more than adequate to assess endogenous eicosanoid metabolism in small (25- to 30-mg) amounts of tissue. The results were expressed as ng of eicosanoid per mg of protein.

Determination of Celecoxib Levels in Mouse Tissues by LC/MS/MS

Following 2 weeks of control or celecoxib supplemented diet mice were euthanized. The colons were opened and washed with ice cold PBS. Mucosa from the distal 6 cm of mouse colon was then gently scraped, snap frozen in liquid nitrogen, and stored at −80° C. for analysis. Approximately 10 mg of frozen tissue was ground to a fine powder using a liquid-nitrogen-cooled mortar (Fisher Scientific Co., Fair Lawn, N.J.). The samples were then transferred to microcentrifuge tubes and three volumes of ice-cold PBS buffer were added before further homogenization of the sample with ultrasonic tissues processor (Masonix). An aliquot (100 µl) of homogenate was transferred to a glass tube (13×100 mm). To the homogenate, 2 ml of hexane:ethyl acetate (1:1, v/v) was added; the mixture was vortex mixed for 5 min. and then centrifuged at 4000 rpm at 5° C. for 5 min. The extraction was repeated twice and the upper organic layer was collected, pooled and evaporated to dryness under a stream of nitrogen at room temperature. The sample was then reconstituted in 200 µL of methanol: 10 mM ammonium acetate, pH 8.5 (1/1. v/v). The celecoxib level in the samples was determined by LC/MS/MS. The LC/MS/MS was operated under the same condition as described for measurement of $PGE_2$ with minor changes. Briefly, ten microliters of the sample was injected on a Luna 3 um phenyl-hexyl 2×150 mm analytical column (Phenomenex). Celecoxib was detected and quantified by operating the mass spectrometer in electrospray negative ion mode and monitoring the transition m/z 380.2>316.1. Quantification was done by comparing the sample peak areas to a standard curve and concentration of celecoxib was normalized by protein concentration. Preliminary studies in which celecoxib was spiked into control normal mouse samples demonstrated that under the above conditions drug recovery consistently exceeded 95% over a wide concentration range.

15-PGDH Western Blot Analysis

Western assay of 15-PGDH was done as described previously, using conditions in which the assay is in the linear range (Yan, M. et al., (2004) *Proc Natl Acad Sci USA* 101, 17468-73). Mucosa was collected from the distal 6 cm of the colon by scraping, snap freezing in liquid nitrogen and storage at 80° C. Tissue lysates were prepared by pipetting in RIPA buffer (Upstate Biotechnology, Lake Placid, N.Y.) (50 mM Tris.HCL/1% Nonidet P-40/0.25% Na-deoxycholate/150 mM NaCl/1 mM EDTA/1 mM PMSF) supplemented with protease inhibitor mixture (Roche, Indianapolis, Ind.), were separated on 12% SDS/PAGE Ready Gels (Pierce, Rockford, Ill.) (30 µg per lane), and transferred to Immobilon polyvinylidene difluoride membrane (Millipore, Billerica, Mass.). The blots were blocked with 5% milk, probed with monoclonal anti-PGDH antibody at a 1:200 dilution (equaling 9.5 µg/ml) (Yan, M. et al., (2004) *Proc Natl Acad Sci USA* 101, 17468-73) and with anti-actin antibody (Sigma-Aldrich, St. Louis, Mo.) at a 1:2000 dilution, developed by using horseradish-peroxidase-conjugated anti-mouse trueblot antibodies (eBiosciene, San Diego, Calif.), visualized by using an Enhanced Chemiluminescence Plus detection kit (Amersham Biosciences, Piscataway, N.J.), following the manufacturer's instructions, and then scanned on a PhosphorImager (Molecular Dynamics, CA).

Human Subjects

We performed an IRB approved prospective, randomized trial of the NSAID, celecoxib, for prevention of sporadic colorectal adenomas (Bertagnolli, M. M. et al., (2006) *N Engl J Med* 355, 873-84). In this study, known as the Adenoma Prevention with Celecoxib (APC) Trial, 2035 patients with a history of colorectal adenomas were randomized to receive either placebo, celecoxib 200 mg twice daily, or celecoxib 400 mg twice daily, and were followed for 36 months. Celecoxib at either dose significantly reduced the incidence of adenomas detected at the end of the 36 month surveillance interval. A subset of patients on the APC trial also underwent a separate pre-treatment endoscopic procedure prior to initiating celecoxib use, during which biopsies of normal rectal mucosa were obtained. Mucosal specimens (2 mm diameter) were flash frozen in liquid nitrogen and stored at –80° C. until assay for 15-PGDH.

Human 15-PGDH Transcript Measurement

RNA was isolated from colon mucosal biopsies using an RNAqueous® kit (Ambion, Austin, Tex.) following the manufacturer's recommended protocol with minor alterations. Briefly, approximately 10 mg of frozen tissue was ground to a fine powder using a liquid-nitrogen-cooled mortar. The samples were then transferred to microcentrifuge tubes containing 400 µl of Lysis/Binding solution. Each sample was then passed through a 26-gauge needle several times until no longer viscous and then loaded onto a filter cartridge for the subsequent washing steps. RNA from each sample was eluted from the filter cartridge using 40 µl of Elution Solution followed by another elution with 20 µl of Elution Solution, for a pooled elution volume of 60 Concentration and quality of the RNA samples were determined using a ND-1000 Spectrophotometer (Nanoprop, Wilmington, Del.) and 500 ng of sample was used for cDNA synthesis and subsequent real-time PCR assays for 15-PGDH. cDNA was synthesized using AMV Reverse Transcriptase (Roche, Indianapolis, Ind.) following the manufacturer's recommended protocol. Real-time PCR measurement of 15-PGDH was performed using the human 15-PGDH Taqman Probe/Primer kit Hs00168359_m1 from Applied Biosystems (Foster City, Calif.) and 1×IQ Supermix from Bio-Rad (Hercules, Calif.), and detected in an Icycler™ optical module (Biorad, Hercules, Calif.) (Yan, M. et al., (2004) *Proc Natl Acad Sci USA* 101, 17468-73). A 25 ul reaction mix contained a 1:20 dilution of primer/probe in 1× Supermix (Bio-Rad, CA). Thermal cycling was initiated at 95° C. for 3 min, followed by 50 cycles of 95° C. for 15 sec and 60° C. for 1 min. Cytokeratin 20 (Krt20), a marker of colonic epithelial cell mass, was used as the endogenous control and was amplified using the human Krt20 TaqMan primer/probe kit Hs00300643_m1 from Applied Biosystems and 1×IQ Supermix, with PCR initiated at 95° C. for 10 min, followed by 50 cycles of 95° C. for 15 sec and 60° C. for 1 min. The level of 15-PGDH RNA was determined as the ratio of 15-PGDH:Krt20=2 exp $(CT_{PGDH}-CT_{Krt20})$. Plotted values of 15-PGDH represent numerical averages of 15-PGDH levels assayed from three independent reverse transcription reactions. Additionally, for each reverse transcription reaction, $CT_{Krt20}$ and $CT_{PGDH}$ were determined as the average values obtained from three independent real-time PCR reactions.

Statistical Analyses

Prostaglandin and celecoxib levels were log transformed in order to be approximately normally distributed for analysis with a generalized linear regression model with contrasts, generating two-sided P-values. Tumor numbers in AOM-treated mice were analyzed using a negative binomial generalized linear model with contrasts, generating two-sided P-values. Results of all mouse studies in the manuscript are presented as mean values±standard errors of the mean. In humans, associations between presence or absence of tumor relapse and 15-PGDH level (treated as a continuous variable) was analyzed using a negative binomial generalized model with contrasts, generating a two-sided P-value (P=0.04). Comparison of median 15-PGDH levels in individuals who relapsed versus those who did not relapse was also done using a Wilcoxon signed-rank test, generating a one-sided P-value (P=0.04) for the pre-specified model that individuals with lower 15-PGDH levels would be celecoxib resistant. And, association between presence or absence of relapse in individuals and 15-PGDH dichotomized by the population mean was done using a Poisson generalized linear model with contrasts, generating a two sided P-value (P=0.03). Association between numbers of recurrent adenoma tumors in celecoxib treated individuals and 15-PGDH levels dichotomized either by the population median or the population mean, was analyzed using a Poisson generalized linear model with contrasts, generating two-sided P-values (respectively P=0.01 and P=0.001).

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of identifying subjects who would be responsive to non-steroidal anti-inflammatory drug (NSAID) therapy, comprising:
   (i) obtaining a biological sample from said subject;
   (ii) measuring 15-hydroxyprostaglandin dehydrogenase (15-PGDH) levels or 15-PGDH activity, and
   (iii) if the 15-PGDH levels or activity in said sample are normal or increased, administering to said subject an NSAID therapy wherein said NSAID therapy treats colon neoplasia or reduces the risk of developing colon neoplasia.

2. The method according to claim 1, wherein the reference level or activity of 15-PGDH is measured from a healthy subject, or a subject known to be responsive to NSAID therapy.

3. The method according to claim 1, wherein said colon neoplasia is colon adenoma.

4. The method according to claim 1, wherein said colon neoplasia is colon cancer.

5. The method according to claim 1, wherein said NSAID therapy treats pain disorders, inflammatory disorders, and immunologic disorders.

6. The method according to claim 1, wherein the sample is a colonic tissue.

7. The method of claim 1 wherein the sample is a bodily fluid selected from blood, serum, plasma, a blood-derived fraction, stool, urine, and a colonic effluent.

8. The method of claim 1, wherein said NSAID therapy is the administration of celecoxib to said subject.

9. The method of claim 1, wherein said NSAID therapy is the administration of aspirin to said subject.

10. A method of determining whether a subject is predisposed to developing resistance to a non-steroidal anti-inflammatory drug (NSAID) therapy, comprising:
    (i) obtaining a biological sample from said subject; and
    (ii) measuring 15-hydroxyprostaglandin dehydrogenase (15-PGDH) levels or 15-PGDH activity; and
    (iii) if the 15-PGDH levels or activity in said sample are reduced, administering to said subject an NSAID therapy and an agent that induces 15-PGDH levels or activity, wherein said agent is not a Prox-1 suppressor and said NSAID therapy treats colon neoplasia or reduces the risk of developing colon neoplasia.

11. The method of claim 10, wherein said agent is erlotinib.

12. The method of claim 10, wherein said agent is butyrate.

13. The method of claim 10, wherein said NSAID therapy is the administration of celecoxib to said subject.

14. The method of claim 10, wherein said NSAID therapy is the administration of aspirin to said subject.

15. A method of identifying a subject who is at risk for developing colon neoplasia, comprising:
    (i) obtaining a colon tissue sample from said subject;
    (ii) measuring 15-hydroxyprostaglandin dehydrogenase (15-PGDH) levels or 15-PGDH activity;
    (iii) comparing the 15-PGDH levels or activity in said subject to at least one control sample, and; and,
    (iv) identifying the subject as at risk for developing colon neoplasia if said subject has a level or activity of 15-PGDH that is less than 50% of the level or activity of 15-PGDH from said at least one control sample.

16. The method of claim 15, wherein if said subject has a level or activity of 15-PGDH that is less than 50% of the level or activity of 15-PGDH from the control sample, than said method comprises the further step of administering to said subject an NSAID therapy and an agent that induces 15-PGDH levels or activity, wherein said agent is not a Prox-1 suppressor.

* * * * *